United States Patent [19]

Ghilardi et al.

[11] 3,960,476

[45] June 1, 1976

[54] LYOPHILIZED AND SPRAY DRIED DYES

[76] Inventors: Giuliana Ghilardi, 52, Rue Michel-Ange, Paris; Pierre Boré, 197, Avenue Daniel Perdrige, 93 Montfermeil; Jean-Francois Grollier, 19, Rue de Dantzig, Paris, all of France

[22] Filed: Apr. 15, 1974

[21] Appl. No.: 461,261

Related U.S. Application Data

[63] Continuation of Ser. No. 120,353, March 2, 1971, abandoned.

[30] Foreign Application Priority Data

Oct. 19, 1970  Luxemburg ............................. 60449
Feb. 15, 1971  Luxemburg ............................. 61890

[52] U.S. Cl. ........................................ 8/10.1; 8/10.2
[51] Int. Cl.$^2$ ........................ A61K 7/12; A61K 7/13
[58] Field of Search ............................. 8/10.1, 10.2

[56] References Cited
UNITED STATES PATENTS

| | | | |
|---|---|---|---|
| 2,875,769 | 3/1959 | Rosmarin et al. | 8/10.2 |
| 3,337,411 | 8/1967 | Wilmsmann | 8/10.2 |
| 3,415,608 | 12/1968 | Tucker | 8/10.2 |
| 3,563,684 | 2/1971 | Charle et al. | 8/10.1 |

FOREIGN PATENTS OR APPLICATIONS 917,840  2/1963  United Kingdom .................... 8/10.2

*Primary Examiner*—Leonard Schenkman

[57] ABSTRACT

A process for producing a dye in powder form involves reacting an oxidation agent with an oxidation base in an aqueous alkaline preferably ammoniacal medium having a pH ranging from 8 to 13 at a temperature and during a period of time allowing at least a partial oxidation, preferably between 15°–30°C for a period of about 5 minutes to 30 hours and lyophilizing or spray-drying the resulting reaction product. The resulting dye can be used to color keratinic fibers, especially human hair.

17 Claims, No Drawings

LYOPHILIZED AND SPRAY DRIED DYES

This is a continuation of application Ser. No. 120,353 filed March 2, 1971 now abandoned.

This application relates to processes for the preparation of a lyophilisate or spray-dried dyestuff product from an oxidation base and optionally with a coupling agent and their use in dyeing keratinic fibers, especially human hair.

The use of dye compositions containing oxidation dyes in the presence of an oxidizing agent or due compositions containing direct dyes for the dyeing of keratinic fibers, especially human hair, is known.

In those processes which make use of oxidation dyes, the dye composition is generally prepared at the time of application to the hair by the addition of an oxidizing agent such as hydrogen peroxide, to an ammonia solution of one or more oxidation bases that are diamines, diaminophenols or aminophenols with amino or hydroxy groups in the para or ortho position with reference to each other, such as paraphenylene diamines, paraaminophenols or derivatives thereof, or to a mixture of such bases with coupling agents or couplers which are metadiamines, metaaminophenols and metadiphenols, or derivatives of these compounds. Such processes permit the attainment of a variety of shades that resist washing and that give complete satisfaction, aesthetically. However, this use of a dye composition containing ammonia and hydrogen peroxide runs the risk of deleteriously altering the hair fiber if these compositions are not accurately measured or if the composition is not essentially perfectly homogeneous. Moreover, the use of paraphenylene diamines can cause allergic reactions on the scalp.

In those dyeing processes that utilize direct dyes, a solution or a dispersion of the direct dyes is simply applied to the hair. The results that are obtained are normally less satisfactory than dyeings obtained with oxidation dyes since the affinity of direct dyes for hair is weaker. Dyeing processes involving the use of direct dyes give, ordinarily, more raw coloring which is less regular and the shades achieved are generally less natural. Besides, the coloration achieved with direct dyes is less stable to washing. On the other hand, the use of direct dyes generally presents no danger and their application to the hair does not entail any risk of deleteriously affecting the hair fiber itself.

The applicants have now discovered a process for dyeing keratinic fibers, especially human hair, that combines the advantages of oxidation dyes and direct dyes, without the known disadvantages inherent in the use of either, applicants' process being characterized in that the dyeing is effected with use of a dye composition that contains a dye in powder form prepared from one or more oxidation bases and optionally one or more conventional couplers, the oxidation base being subjected for a certain period of time to the action of an oxidizing agent and the resulting reaction product being dried to powder form.

The dye in powder form can be prepared from a reaction mixture that contains an oxidation base and when desired, a coupler, by lyophilization, or by spray-drying, in some instances, especially when the dyes that are formed are not stable to heat, it is particularly advantageous to prepare the dye in powder form by a lyophilization procedure.

Lyophilization can have the further advantage of allowing separation of the free radicals.

The dye in powder form that is obtained by lyophilization is called the lyophilizate or freeze-dried dye and the dye in powder form obtained by spray-drying is called spray-dried dye. The thus produced dyes are used to color hair in much the same fashion as conventional direct dyes.

The dye in powder form obtained by lyophilization or by spray-drying has a water solubility that is generally greater than 5 g/liter, and can be as high as 100 g/liter, or more.

While aqueous, or alcoholic, or aqeuous alcoholic solutions prepared from such a dye in powder form can be stable, in most cases their stability is somewhat limited and it is generally preferable to prepare the dye composition at the time it is to be applied to the hair.

The dyeing effected with a dye composition made from a freeze-dried dye or spray-dried dye of this invention after being applied to a head of hair and when using a direct dyestuff, give a result of comparable quality to that produced with a dyeing composition containing the same base and the same coupling agent in the same proportions as present in the solution from which the powder of the composition of the present invention was prepared where the composition is applied after adding ammonia and hydrogen peroxide to the dyeing composition. Hence the present invention makes it possible, by using the method of application or direct dyestuffs, to achieve a quality of dyeing comparable to that obtained with oxidation dyestuffs, without the disadvantages of the latter.

Thus, the present invention has as one object a process for preparing a freeze-dried dye or a spray-dried dye from an aqueous alkaline solution such as a sodium carbonate solution and preferably from an ammoniacal solution containing the reaction product resulting from the reaction of an oxidizing agent on an oxidation base, optionally in the presence of one or more couplers.

Another object of the present invention is to provide lyophilized and spray-dried dyes.

Another object of the present invention is to provide mixtures of lyophilized and spray-dried dyes with other dyestuffs and cosmetic ingredients, referred to hereinafter as complex powders.

Still another object of the present invention is to provide a dye composition containing said lyophilized or spray-dried dye.

A further object of the invention is to provide a process for dyeing keratinic fibers using these dye compositions.

In accordance with one embodiment of the present invention, a lyophilized dye can be prepared by reacting at least one oxidation base optionally with one or more coupling agents the molar ratio of coupling agents : oxidation bases being between about 0:1 to 10:1 and preferably between 0:1 to 2:1 in an aqueous alkaline, for example sodium carbonate solution and preferably in ammoniacal solution open to ambient atmosphere and having a pH ranging from about 8 to 13 at a temperature and during a period of time allowing at least partial oxidation, generally a temperature between about 15°–30°C for a period of about 5 minutes to 30 hours is used and lyophilizing the resulting reaction mixture to produce said dye in powder form. Generally, the molar ratio of oxidizing agent to oxidation base will range between about 0.1:1 to 20:1, preferably an excess of oxidizing agent is used. In this procedure, lyophilizing comprises freezing the reaction mixture at a temperature ranging from about –60°C to −200°C, and generally from −60°C to −90°C, thereby terminating the reaction and subliming said reaction mixture at a temperature of about −30°C to −50°C, preferably below −35°C at a pressure of about 0.1 mm.Hg to 0.01 mm. Hg. The step of freezing the reaction mixture, of course, can be implemented at any desired stage of the reaction, the process of which can be followed by chromatographic analysis. Following lyophilization, if desired or necessary to eliminate any residual moisture content, the lyophilized dye can be desorbed at a temperature ranging between 15° to 60°C, at a pressure ranging between 10 mm to 0.001 mm.Hg. preferably about 0.01 mm. Hg.

Conveniently, the frozen reaction mixture is sublimated in a conventional apparatus available commercially under the trade name USIFROID SMJ (Rieutord process) provided with an internal condenser, although it will be appreciated that any conventional freeze-drying means can be employed.

As stated above, when required, desorption can be effected at a temperature between 15 and 60°C under very low pressure, generally of the order of about 0.005 mm.Hg to about 0.01 mm. Hg, the temperature of the condenser in the apparatus employed being held at about −200°C to.−70°C and preferably at about −70°C. The total duration of the lyophilization under these conditions is of the order of about 10 to 30 hours and the product of lyophilization thus obtained is a powder having a very high specific surface area.

In accordance with another embodiment of the present inventinn a spray-dried dye can be prepared by reacting at least one oxidation base optionally with one or more coupling agents the molar ratio coupling agents : oxidation bases being between about 0:1 to 10:1 and preferably between 0:1 to 2:1 with a molar excess of an oxidizing agent in an aqueous alkaline for example sodium carbonate solution and preferably in ammoniacal solution open to ambient atmosphere and having a pH ranging from about 8 to 13 at a temperature and during a period of time allowing at least a partial oxidation generally a temperature between about 15°–30°C and a period of about 5 minutes to 30 hours and spray-drying the resulting reaction mixture to produce said dye in powder form.

In spray-drying, the resulting reaction can be charged, in finely divided form, for instance, in atomized form, into a current of heated air introduced into a drying chamber. The current of air can have an inlet temperature ranging from about 80°–350°C. preferably between 150°–300°C and optimumly its temperature is about 230°C. The outlet temperature of the air is maintained at about 50°–200°C, preferably, about 80°–130°C and optimumly, its temperature is about 100°C.

Subsequent to the above spray-drying operation, when desired or necessary to eliminate residual moisture content, the spray-dried product can be treated or desorbed at a temperature ranging between 20° to 80°C, preferably at about 40°C at a pressure ranging between 1 mm.Hg to 0.01 mm.Hg for a period of about 2 to 40 hours.

Further, in accordance with the present invention, the ammonia and/or hydrogen peroxide can be eliminated from the reaction mixture prior to freezing or spray-drying the same.

Representative oxidation bases utilized in the process of the present invention are those generally utilized in dye processes in which oxidation dyes are used. Illustrative of such bases are those listed in the Colour Index, 2nd edition, 1956, vol. 3, pages 3593–3601. For example the following bases can be employed: paratoluylene diamine, paraphenylene diamine, N,N-dimethyl paraphenylene diamine, methyl paraphenylene diamine, chloroparaphenylene diamine, 2-methoxy 5-methyl paraphenylene diamine, 2,6-dimethyl 3-methoxy para phenylene diamine, tetramethyl paraphenylene diamino, 2-methoxy paraphenylene diamine, para aminophenol, 2,6-dimethyl para aminophenol, 2,4-diamino anisole, 2-methyl para aminophenol and 1-methoxy 2,5-dimethyl paraphenylene diamino hydrochloride.

Representative couplers used in the process of this invention are those that are customarily used in dye processes using oxidation dyes. As non-limiting examples there can be mentioned metaphenylene diamine, 2,4-diamino anisole (meta diamino anisole) and the sulfate and hydrochloride thereof, 2,4-diamino toluene, meta aminophenol, 6-methyl 3-amino phenol, N-methyl meta aminophenol and its hydrobromide, 4-methoxy 3-amino phenol, resorcinol, and alpha naphtol.

It is to be noted that 2,4-diamino anisole which is a meta-diamine and consequently has the structure of a coupling agent, may, in certain cases and, in particular, when used by itself, act as a base.

There can be added to the reaction mixture, as fillers oligo peptides such as hydrolysis products of proteins, amino acids, polymers, i.e. polyvinyl pyrrolidone (PVP) having a molecular weight ranging between 40,000 to 360,000 the preferred molecular weight being 40,000 or copolymers such as the copolymer of polyvinyl pyrrolidone and vinyl acetate (MW = 40,000 − 160,000) 70% : 30% to 30% : 70%, the preferred proportion being 60% : 40% having a viscosity of 3,3 to 4 centipoises in 5% solution in ethanol; or copolymers of crotonic acid and vinyl acetate 90% : 10% having a molecular weight of 40,000 to 200,000 and preferably of 50,000 and a viscosity of 7 to 9 centipoise in 5% solution in tetrachlorethane.

This addition has the effect of increasing the total volume and ensuring a very high degree of reproducibility of the characteristics of the products of lyophilization that are obtained and of its dyeing properties. Generally, the total amount of filler employed will rage between about 1 to 20 and preferably 5 weight percent of the total reaction mixture.

Representative protein hydrolysis product include : hydrolized keratine products sold under the name "Keratin Hydrolysate" by GEO, mixtures of aminoacids sold under the name "Aminoacid Complex" by GEO, hydrolysed casein sold under the name "Casein Hydrolysate" by GEO, and the following products known in the trade under the commercial designations "Capilane KS" by Sandoz, "Polypeptide Wilson W.S.P. 250" and "Polypeptide L.S.N." by Stepan Chemicals.

Representative aminoacids that can be employed include alanine, glycine, glutamic acid and cystine.

It will be appreciated that the reaction can be stopped either when the oxidation of the mixture has completely run its course, or at an intermediate stage, so that the product of lyophilization or spray-drying will still contain a certain amount of base and coupler when employed. In this case, a product of lyophilization or spray-drying is obtained that can then be utilized partly as a direct dye and partly as an oxidation dye which allows the production of a substantial varied range of dye compositions.

The lyophilizate or freeze-dried dye and the spray-dried dye may be mixed with other liophilizates or spray-dried dyes and with polymers i.e. polyvinyl pyrrolidone (PVP) having a molecular weight ranging between 40,000 to 360,000 or copolymers such as the copolymers of PVP and vinyl acetate 70% : 30% to 30% : 70%, the preferred proportion being 60% : 40% having a viscosity of 3. 3- 4 centipoises in 5% in ethanol, or copolymer of crotonic acid and vinyl acetate 90% : 10% having a molecular weight ranging from 40,000 to 200,000 and preferably 50,000 having a viscosity of 7 to 9 centipoises in 5% solution in tetrachlorethane and mixtures thereof, optical bleaching agents and/or ingredients conventionally employed in hair dye compositions such as thickeners and/or other dyestuffs which may be acid, basic or direct, soluble or disperse dyestuffs such as anthraquinone, azo or nitro dyestuffs or metal complex dyestuffs or other indamines, indoanilines and indophenols. The mixtures thus obtained, referred to hereinafter as "complex powders", also allow dyeing solutions and dispersions for the hair to be prepared.

Thus, in accordance with another embodiment of the present invention there is provided a novel dye composition for coloring keratinic fibers, especially human hair, comprising a solution in a solvent selected from the group consisting of water, alkanol and mixtures thereof of dyes in powder form selected from the group formed by a lyophilized dye, a spray-dried dye produced in accordance with the processes disclosed above and mixtures thereof, said dye being present in amounts of about 0.0005–5 percent by weight of said composition, and said composition having a pH ranging from about 2.5–10.

The alkanol employed generally is a lower alkanol, for instance, ethanol or isopropanol and when used in admixture with water, the alkanol can be present in amounts of about 1 to 96 weight percent of the resulting aqueous alkanol solution.

The pH of the dye composition of this invention can be adjusted to the values given above by admixing therewith effective amounts of a compatible mineral or organic base such as triethanolamine or ammonia, or an effective amount of an acidic substance such as lactic acid or citric acid. Obviously, other conventional substances normally used to adjust the pH of cosmetic preparations can also be used.

The novel dye compositions of this invention can also contain conventional film forming resins, optical bleaching agents or other ingredients customarily used in cosmetics such as thickeners. Additionally acid, basic or direct dyes as well as disperse dyes such as anthraquinone dyes, azo dyes, nitrated dyes or metalliferous complex dyes can be included in the dye compositions of this invention. Moreover, the novel dye compositions may also include other indamines, indoanilines and indophenols than those formed during the oxidation preceding the freezing or the lyophilization or the spray-drying.

Representative film forming resins that can be employed in the dye compositions can include, for instance, polyvinyl pyrrolidone having a molecular weight ranging from 40,000 to 360,000, copolymer of vinyl pyrrolidone and vinyl acetate having a molecular weight ranging from 40,000 to 160,000, a copolymer of crotonic acid and vinyl acetate having a molecular weight ranging from 40,000 to 200,000 and mixtures thereof. Generally, the film forming resin, when used, will be employed in amounts ranging from about 0 5 to 4 weight percent of the dye composition.

Representative indamines, indoanilines and indophenols that can be combined with the powdered dyes of this invention can have the general formula

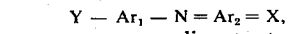

or a corresponding tautomeric form thereof wherein $Ar_1$ and $Ar_2$ each independently represent a hydrocarbon aromatic nucleus and a heterocyclic aromatic nucleus, each optionally substituted with a member selected from the group consisting of amino, hydroxy, lower alkoxy, lower alkyl, acylamino and halogen such as chlorine and bromine, Y represents a member selected from the group consisting of a hydroxy and

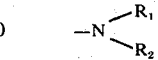

wherein $R_1$ and $R_2$ each independently represent a member selected from the group consisting of hydrogen, lower alkyl, hydroxy lower alkyl and amino lower alkyl with amine function optionally substituted or acylated, and X represents a member selected from the group consisting of oxygen, imine and iminium groups, or salts of these compounds.

In this context, lower alkyl and lower alkoxy mean those having 1–4 carbon atoms.

It will be observed that the nomenclature adopted for these compounds corresponds to a numering of the aromatic cycles $Ar_1$ and $Ar_2$ that, in the case of benzene rings, is the following:

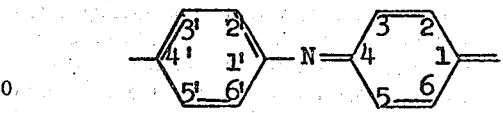

Representative indamines that can be used in the present invention, are N-[(4'-dimethylamino)phenyl] 3-amino 6-methyl benzoquinone diimine, N-[4'-amino 2'-methoxy 5'-methyl)phenyl] 2-aza-3-amino benzoquinone diimine monoacetate, double chloride of zinc and of N-[(ethyl acetylaminoethyl) 4'-amino phenyl ] 3-amino methoxy benzoquinone diimine, N-[4'-amino 2'-methoxy 5'-methyl)phenyl] 3-amino 6-methyl benzoquinone diimine monoacetate, and the double chloride of zinc and N-[(ethyl beta acetyl aminoethyl) 4'-aminophenyl] 3 hydroxybenzoquinone imine N',N'-diethyliminium.

Representative indoanilines that can be used in the present invention are, for instance N-[(4'-dimethylamino) phenyl]2,6-dimethyl benzoquinone imine, N-[(4'-dimethylamino) phenyl]2,5-dimethyl benzoquinone imine, N-[(4'-amino 2'-methoxy 3'.5'-dimethyl)-phenyl] 2,6-dimethyl benzoquinone imine, N-[(4'-amino 2'-methoxy 3',5'-dimethyl)phenyl] 2,5-dimethyl benzoquinone imine, N-[(4'-dimethylamino)phenyl] 3-amino 6methyl benzoquinoneimine, N-[4'-amino 2'-methoxy)phenyl] 3-amino 6-methyl benzoquinone imine, N-[(4'-amino 2'-methoxy 5'-methyl)phenyl] 3-acetylamino 6-methyl benzoquinoneimine, N-[(4'-hydroxy)phenyl] 3-amino-6-methoxy-benzoquinone diimine, N-[(4'-hydroxy)phenyl] 3-aminobenzoquinone diimine and N-[(4'-amino 3'-chloro) phenyl] 3-amino 2,6-dimethyl benzoquinone imine.

Representative indophenols that can be used in the present invention include N-[(4'-hydroxy)phenyl]2,6-dimethyl benzoquinone imine, N-[(4'-hydroxy)phenyl] 2,5-dimethyl benzoquinone imine, N-[(4'-hydroxy)-phenyl] 3-amino-6-methyl benzoquinone imine and N-[(4'-hydroxy 3',5'-dimethyl)phenyl] 2,6-dimethyl benzoquinone imine. Other indophenols, indamines and indoanilines suitably employed are those disclosed in commonly assigned U.S. Patent applications Ser. No. 45,564, filed June 11, 1970, Ser. No. 49,905, filed June 25, 1970, Ser. No. 52,739, filed July 6, 1970, Ser. No. 97,395, CIP of Ser. No. 45,564, filed Dec. 11, 1970, Ser. No. 100,433, CIP of Ser. No. 49,905, filed Dec. 21, 1970, and Ser. No. 161,887, CIP of Ser. No. 52,739, filed July 12, 1971. Generally, the amount of indophenol, indoaniline or indamine added to in the dye composition will range between about 1 to 99 Weight percent of the total weight of the powder.

The dyes of the present invention, in powder form, alone or in admixture with other adjuvants or other dyes, can be compressed into tablet form, thereby facilitating their packaging as well as their use in preparing, at the time of application, the novel dye composition of this invention.

As mentioned the lyophili ate or spray-dried dye and complex powders or tablets of the present invention allow dyeing solutions and dispersions for hair to be prepared. The lyophili ate or (freeze-dried dye) or spray-dried dye may be added to an appropriate cosmetic carrier containing adjuvants such as cosmetic resins, thickening agents, optical bleaching agents, perfumes, sun filters and/or other ingredients.

As stated before, it is generally desirable to prepare the dye composition just before use since an advantage of this procedure is the achievement of obtaining excellent reproducibility of the colors imparted to the hair.

The novel dye compositions can also be provided as a pressurized sprayable aerosol comprising a solution of the lyophilized or spray-dried dye in a lower alkanol solution in admixture with an aerosol propellant, such as a fluorinated hydrocarbon. Representative propellants include dischloro-difluromethane, trichloromono-fluoromethane and their mixtures. Generally the propellant will be present in amounts of about 50 to 90 weight percent of the total aerosol composition, the remainder being essentially the dye-alkanol solution in which said dye is present in amounts of about 0.001 to 5 percent by weight thereof. Conventional aerosol containers are employed in packaging the above composition under pressure.

The novel dye compositions can also be used as a two component pack which comprises, as the first component, a freeze-dried dye or a spray-dried dye produced in accordance with the processes discussed above, or mixtures thereof with other dyestuffs and cosmetic ingredients referred to hereabove as "complex powders" and as the second component an appropriate cosmetic carrier optionally containing at least one cosmetic resin, thickening agent, optical bleaching agent perfumes, sun filter or other ingredient conventionally employed in hair dye compositions.

The freeze-dried or spray-dried dye made in accordance with the present invention can also be employed to produce a "bleaching dye" composition by admixing therewith hydrogen peroxide in an ammoniacal solution. Such a "bleaching dye" composition has a pH ranging from about 8 to 12 and about 2 to 6 weight percent hydrogen peroxide. The dye of this invention is present therein in amounts ranging from about 0.0005–5% by weight of the total composition.

The freeze-dried or spray dried dye of this invention can also be employed to produce a "tinting" dye composition by including therein an oxidation dye or base as defined above. Generally the oxidation dye or base will be present in amounts ranging from about 0.05 to 4 percent by weight of the total composition.

Conventional oxidation hair dyestuffs that can be used are, for instance, the oxidation bases defined above including those set forth in the above referred to portions of Colour Index. Representative of such oxidation dyestuffs are paraphenylene diamine, 2,5-toluene diamine sulfate, chloro para phenylene diamine sulfate, nitro para phenylene diamine, 1,2,4-triamine benzene dihydrochloride, para amino diphenyl amine, ortho phenylene diamine, 4-chloro ortho phenylene diamine, 4-nitro ortho phenylene diamine, 5-chloro 3-nitro ortho phenylene diamine, para aminophenol, 4-amino 2-methyl phenol sulfate, 4-amino 3-methyl phenol, 4-amino 2-nitro phenol, 2,4-diaminophenol hydrochloride, para methyl amino phenol sulfate, ortho amino phenol, 4-chloro-2-amino phenol, 4-nitro 2-amino phenol, 5-nitro 2-aminophenol, 4,6-dinitro 2-aminophenol, 6-chloro 4-nitro 2-aminophenol hydrochloride, 4-amino diphenylamine, 2,4-diamino diphenylamine, 4,4'-diamino diphenylamine sulfate, meta phenylene diamine, chloro meta phenylene diamine, nitro meta phenylene diamine, meta toluylene diamine, 2,4-diamino anisol sulfate, meta aminophenol, 3,5-diamino phenol hydrochloride, diethyl meta amino phenol and para amino ortho cresol.

Another embodiment of the present invention is the provision of a process for dyeing keratinic fibers, and especially human hair, comprising applying to said hair in amounts effective to color the same, the novel dye compositions as defined above. The hair, optionally, can be washed and dried prior to or subsequent to the application of the dye composition, it being observed, that the dye composition can be used as a hair setting lotion. In those instances where the dye composition includes hydrogen peroxide as a component thereof, the dye composition is permitted to remain in contact with the hair for a period of about 5 to 40 minutes. The thus treated hair is thereafter rinsed, washed and dried.

The following examples are given to illustrate the present invention:

EXAMPLES OF PREPARING LYOPHILIZED AND SPRAY DRIED DYES

EXAMPLE 1

A lyophilic product is prepared in the following manner: There is left standing in the open air at a temperature of 20°C for a period of 16 hours in "penicillin" type bottles filled to a depth of 7 mm, a mixture comprising 100 ml of 20-volume hydrogen peroxide, and 100 ml of a solution which contains 0.01 moles paratoluylenediamine, 0.005 moles 2,4-diaminoanisole sulfate, 5 g of the hydrolysis product of proteins sold under the designation "Anhydrous LSN Polypeptides" by the "STEPAN CHEMICAL" Company, and 1 ml of ammonia (22° Be). The reaction is stopped by freezing to −60°C, and the bottles are introduced into a sublimation apparatus of the type "USIFROID SMJ (Rieutord Process) provided with a condenser inside the vessel. Sublimation is effected at a temperature below −30°C and at a pressure of 0.1 mm Hg for 20 hours. Desorption of the product is then effected at +30°C under vacuum of 0.01 mm Hg, the temperature of the condenser being held at −70°C. There is obtained a substance which by homogenization yields a colored powder whose specific surface area is very high.

EXAMPLE 2

The following lyophilic product is prepared: There is left standing at a temperature of 20°C for a period of 3 hours a mixture comprising 100 ml 20-volume hydrogen peroxide and 100 ml of a solution containing 0.1 mole/liter of paratoluylenediamine, 0.1 mole/liter of 2,4-diaminoanisole sulfate, 50 grams/liter of the hydrolysis product of proteins sold under the name "Anhydrous LSN Polypeptides" by the "STEPAN CHEMICAL" Company and 10 ml of ammonia (22°Be). The reaction is stopped by freezing at a temperature of −60°C and the sublimation and desorption treatment is continued as in Example 1. By homogenizing the obtained mass, there is produced a lyophilized colored powder.

EXAMPLE 3

There is left standing in open air at a temperature of about 20°C for 20 minutes in "penicillin" bottles at a depth of 7 mm, the following solution:

| | |
|---|---|
| 2,4-diamino anisole hydrochloride | 4.22 g (0.02 mole) |
| Anhydrous LSN Polypeptide sold by "STEPAN CHEMICAL" company | 5 g |
| Ammonia (22°Be) | 5 cc |
| Hydrogen peroxide, 20 volumes | 50 cc |
| Water, q.s.p. | 100 cc |

The reaction is stopped by freezing to −60°C and then the reaction mixture is sublimated in a lyophilizing apparatus called USIFROID M.S.D. at a temperature of −40°C and at a pressure of 0.05 mm Hg for 24 hours. Desorption is effected at a temperature of +25°C.

Chromatography of the product of lyophilization on a silica layer does not reveal the presence of 2,4-diamino anisole.

EXAMPLE 4

The following solution is left standing in open air at a temperature of about 20°C for 40 minutes in "penicillin" bottles at a depth of 7 mm:

| | |
|---|---|
| Paraaminophenol | 1.09 g (0.01 mole) |
| 2,4-diamino anisole hydrochloride | 2.11 g (0.01 mole) |
| Sodium hydroxide | 0.4 g (0.01 mole) |
| Anhydrous LSN Polypeptide | 5 g |
| Ammonia solution (22°Be) | 5 cc |
| Hydrogen peroxide, 20 volumes | 50 cc |
| Water, q.s.p. | 100 cc |

The reaction is stopped by freezing at −60°C and then the reaction mixture is sublimated in a USIFROID SMJ apparatus at a temperature of −35°C and at a pressure of 0.06 mm Hg for 24 hours. Termination is effected by desorption at a temperature of +25°C.

Chromatography of the produce of lyophilization on a silica layer reveals the presence of a small quantity of paraminophenol and absence of 2,4-diamino anisole hydrochloride.

EXAMPLE 5

There is left standing in open air at a temperature of about 20°C for 40 minutes in "penicillin" bottles at a depth of 7 mm, the following solution:

| | |
|---|---|
| Paraaminophenol | 1.09 g (0.01 mole) |
| 2,4-diaminoanisole hydrochloride | 4.22 g (0.02 mole) |
| Anhydrous LSN Polypeptide | 5 g |
| Ammonia (22°Be) | 5 cc |
| Hydrogen peroxide, 20 volumes | 50 cc |
| Water, q.s.p. | 100 cc |

The reaction is stopped by freezing to −60°C and then the reaction product is sublimated in a USIFROID SMJ apparatus at a temperature of −40°C and at a pressure of 0.05 mm Hg for 24 hours. Termination is effected by desorption at a temperature of +25°C.

Chromatography of the product of lyophilization on a silica layer shows the presence of a small amount of paraminophenol and absence of 2,4-diaminoanisole hydrochloride.

EXAMPLE 6

There is left standing in open air at a temperature of about 20°C for 40 minutes in "penicillin" bottles at a depth of 7 mm, the following solution:

| | |
|---|---|
| Paratoluylenediamine | 1.22 g (0.01 mole) |
| Metaminophenol | 1.09 g (0.01 mole) |
| Anhydrous LSN Polypeptide | 2.5 g |
| Polyvinylpyrrolidone (MW 40,000) | 2.5 g |
| Ammonia (22°Be) | 5 cc |
| Hydrogen peroxide, 20 volumes | 50 cc |
| Water, q.s.p. | 100 cc |

The reaction is stopped by freezing to −60°C and then the resulting mixture is sublimated in a USIFROID SMJ apparatus at a temperature of −50°C and at a pressure of 0.01 mm Hg for 24 hours. Termination is effected by desorption at a temperature of +25°C.

Chromatography of the product of lyophilization on a silica layer reveals the presence of metaminophenol and the absence of paratoluylenediamine.

EXAMPLE 7

Proceeding in the manner outlined in Example 5, the following solution is employed:

| | |
|---|---|
| Paratoluylenediamine | 1.22 g (0.01 mole) |
| Metaminophenol | 1.09 g (0.01 mole) |
| Anhydrous LSN Polypeptide | 5 g |
| Ammonia (22°Be) | 5 cc |
| Hydrogen peroxide, 20 volumes | 50 cc |
| Water, q.s.p. | 100 cc |

Chromatography of the product of lyophilization on a silica layer shows the presence of a small quantity of metaminophenol and the absence of paratoluylenediamine.

EXAMPLE 8

Proceeding in the manner outlined in Example 5, the following solution is employed:

| | |
|---|---|
| Paratoluylenediamine | 2.44 g (0.02 mole) |
| Metaminophenol | 1.09 g (0.01 mole) |
| Anhydrous LSN Polypeptide | 2.5 g |
| Polyvinylpyrrolidone (MW 40,000) | 2.5 g |
| Ammonia (22°Be) | 5 cc |
| Hydrogen peroxide, 20 volumes | 50 cc |

-continued

| | |
|---|---|
| Water, q.s.p. | 100 cc |

Chromatography of the product of lyophilization on silica reveals the presence of paratoluylenediamine and metaminophenol.

EXAMPLE 9

There is left standing in the open air at a temperature of about 20°C for 40 minutes in "penicillin" bottles at a depth of 7 mm, the following solution:

| | |
|---|---|
| Paratoluylenediamine | 1.22 g (0.01 mole) |
| N-methyl metaminophenol hydrobromide | 2.04 g (0.01 mole) |
| Anhydrous LSN Polypeptide | 2.5 g |
| Polyvinylpyrrolidone (MW 40,000) | 2.5 g |
| Ammonia (22°Be) | 5 cc |
| Hydrogen peroxide, 20 volumes | 50 cc |
| Water, q.s.p. | 100 cc |

The reaction is stopped by freezing to −60°C and sublimation is effected in a USIFROID MSD apparatus at a temperature of −40°C and at a pressure of 0.25 mm Hg. Termination is effected by desorption at a temperature of +25°C.

Chromatography of the product of lyophilization on a silica layer shows the presence of very small amounts of paratoluylenediamine and N-methylmetaminophenol.

EXAMPLE 10

There is left in the open air at a temperature of about 20°C for 1 hour in an aluminum can filled to a depth of 8 to 9 mm the following solution:

| | |
|---|---|
| Paratoluylenediamine | 2.44 g (0.02 mole) |
| N-methyl metaminophenol hydrobromide | 2.04 g (0.01 mole) |
| Anhydrous LSN Polypeptide sold by the "STEPAN CHEMICAL" Company | 2.5 g |
| Polyvinylpyrrolidone (MW 40,000) | 2.5 g |
| Ammonia (22°Be) | 5 cc |
| Hydrogen peroxide, 20 volumes | 50 cc |
| Water, q.s.p. | 100 cc |

The reaction is stopped by freezing to −60°C. The reaction mixture is then sublimated in a USIFROID MSD apparatus at a temperature of −40°C and at a pressure of 0.05 mm Hg, followed by desorption at a temperature of +25°C. The operation lasts for 28 hours.

Chromatography of the product of lyophilization on a silica layer does not show any trace whatsoever of paratoluylenediamine nor of N-methyl metaminophenol.

EXAMPLE 11

There is left standing in the open air at a temperature of about 20°C for one hour in "penicillin" bottles filled to a depth of 7 mm the following solution:

| | |
|---|---|
| Paratoluylenediamine | 2.44 g (0.02 mole) |
| 3-amino 4-methoxyphenol | 1.39 g (0.01 mole) |
| Anhydrous LSN POlypeptide sold by the "STEPAN CHEMICAL" Company | 2.5 g |
| Polyvinylpyrrolidone (MW 40,000) | 2.5 g |
| Ammonia (22°Be) | 5 cc |
| Hydrogen peroxide, 20 volumes | 50 cc |
| Water, q.s.p. | 100 cc |

The procedure as described in Example 5 is then followed.

Chromatography of the product of lyophilization on a silica layer does not show any trace of paratoluylenediamine nor of 3-methoxy-4-aminophenol.

EXAMPLE 12

There is left standing in open air at a temperature of about 20°C for 40 minutes in "penicillin" bottles filled to a depth of 7 mm, the following solution:

| | |
|---|---|
| Paratoluylenediamine | 1.22 g (0.01 mole) |
| Resorcine | 1.10 g (0.01 mole) |
| Polyvinylpyrrolidone (MW 40,000) | 5 g |
| Ammonia (22°Be) | 5 cc |
| Hydrogen peroxide, 20 volumes | 50 cc |
| Water, q.s.p. | 100 cc |

The procedures as described in Example 5 are then followed.

Chromatography of the product of lyophilization on a silica layer does not show any trace of paratoluylenediamine nor of resorcine.

EXAMPLE 13

The following solution is allowed to stand in open air at a temperature of about 20°C for 40 minutes, in a "penicillin" bottle filled to a depth of 7 mm:

| | |
|---|---|
| Paratoluylene diamine | 1.22 g (0.01 mole) |
| 2,4-diamino anisole hydrochloride | 2.11 g (0.01 mole) |
| Anhydrous LSN polypeptide | 5 g |
| Ammonia (22°Be) | 5 cc |
| Hydrogen peroxide, 20 volumes | 50 cc |
| Water, q.s.p. | 100 cc |

The reaction is stopped by freezing at −60°C and the mixture is then sublimated in a USIFROID SMJ apparatus at a temperature of −50°C and at a pressure of 0.01 mm. Hg, followed by desorption at a temperature of +25°C. The operation lasts for 24 hours.

Chromatography of the product of lyophilization on a silica layer did not reveal any trace whatsoever of paratoluylene diamine or of 2,4-diamino anisole.

EXAMPLE 14

The following solution is allowed to stand in open air at a temperature of about 20°C for 40 minutes, in a "penicillin" bottle filled to a depth of 7 mm:

| | |
|---|---|
| 1-methoxy 2,5-dimethyl paraphenylene diamine hydrochloride | 1.08 g (0.01 mole) |
| 2,4-diamino anisole | 2.11 g (0.01 mole) |
| Anhydrous LSN polypeptide | 5 g |
| Ammonia (22°Be) | 5 cc |
| Hydrogen peroxide, 20 volumes | 50 cc |
| Water, q.s.p. | 100 cc |

The procedure outlined in Example 5 is then followed.

Chromatography of the product of lyophilization on silica revealed a slight trace of 1-methoxy 2,5-dimethyl paraphenylene diamine but indicated no presence of 2,4-diamino anisole.

EXAMPLE 15

The following solution is allowed to stand in open air at a temperature of about 20°C for 1 hour in a "penicillin" bottle filled to a depth of 7 mm:

| | |
|---|---|
| Paratoluylene diamine | 1.22 g (0.01 mole) |
| Paraaminophenol | 1.09 g (0.01 mole) |

-continued

| | |
|---|---|
| 2,4-diamino anisole hydrochloride | 2.11 g (0.01 mole) |
| Resorcin | 1.10 g (0.01 mole) |
| Meta aminophenol | 1.09 g (0.01 mole) |
| Anhydrous LSN polypeptide | 5 g |
| Ammonia (22°Be) | 20 cc |
| Hydrogen peroxide, 20 volumes | 50 cc |
| Water, q.s.p. | 100 cc |

The procedure described in Example 5 is then repeated. Chromatography of the resulting product of lyophilization on silica revealed the presence of small amounts of paratoluylene diamine, paraaminophenol and resorcin, and some metaaminophenol, but there was no trace of 2,4-diamino anisole.

EXAMPLE 16

The following solution was allowed to stand in the open air for 2 hours:

| | |
|---|---|
| Paratoluylene diamine | 1.22 g (0.01 mole) |
| 2,4-diamino anisole hydrochloride | 2.11 g (0.01 mole) |
| Anhydrous LSN polypeptide | 5 g |
| Ammonia (22°Be) | 5 cc |
| Hydrogen peroxide, 20 volumes | 50 cc |
| Water, q.s.p. | 100 cc |

After 2 hours, there was added to this solution a sufficient amount of a 1 N potassium permanganate solution to eliminate excess hydrogen peroxide by precipitation of manganese oxide. (The potassium iodide test was used to reveal absence of hydrogen peroxide). The precipitate was eliminated by drying. The filtrate was then frozen in a "penicillin" bottle filled to a depth of 7 mm at −60°C. Then the procedure outlined in Example 6 was followed. Silica layer chromatography showed no paratoluylene diamine or 2,4 diamino anisole.

EXAMPLE 17

There is left standing in open air at a temperature of about 20°C for 20 minutes the following solution:

| | |
|---|---|
| 2,4-diaminoanisole hydrochloride | 21.1 g (0.1 mole) |
| Paratoluylenediamine | 12.2 g (0.1 mole) |
| Anhydrous LSN polypeptide sold by "STEPAN CHEMICAL" Company | 25 g |
| Polyvinylpyrrolidone (MW 40,000) | 25 g |
| Ammonia (22°Be) | 50 cc |
| Hydrogen peroxide, 20 volumes | 500 cc |
| Water, q.s.p. | 1000 cc |

At the end of 20 minutes there is added concentrated hydrochloric acid with agitation until the pH of the solution reaches the value of 8 and the reaction mixture is then filtered.

There is then sprayed about 1 liter of the filtrate on a MINOR MOBILE apparatus sold by NIRO ATOMIZER Co. The temperature of the air at the inlet is 220°C and the temperature of the air at the outlet is 98°C.

A more nearly total desorption is effected in a drier over a period of 24 hours at 40°C under a pressure of a few mm mercury.

The atomized product obtained is soluble in water and chromatography of this product on a thin silica layer reveals the presence of indamine as well as the presence of paratoluylenediamine and 2,4-diaminoanisole.

EXAMPLE 18

The solution of Example 17 is allowed to stand in open air at a temperature of about 20°C for 1 hour.

At the end of 1 hour there is added concentrated hydrochloric acid with agitation until the pH of the solution attains the value of 7. The reaction mixture is then filtered, and about 1 liter of the filtrate is sprayed in the same manner outlined in Example 17.

There is obtained an atomized product that is soluble in water and alcohol.

Chromatography of that atomized product on a thin silica layer reveals the presence of indamine as well as the presence of traces of paratoluylenediamine and 2,4-diaminoanisole.

EXAMPLE 19

The solution of Example 17 is allowed to stand in open air at a temperature of about 20°C for 2 hours.

At the end of 2 hours, concentrated hydrochloric acid is added with agitation until pH 7 is reached. The reaction mixture is then filtered and about 500 cc of the filtrate are sprayed in the manner outlined in Example 17.

A water soluble atomized product is obtained.

Chromatography of this product on a layer of silica shows the presence of indamine and the absence of paratoluylenediamine and 2,4-diaminoanisole.

EXAMPLE 20

The following solution is allowed to stand in open air at a temperature of about 20°C for 17 hours:

| | |
|---|---|
| 2,4-diaminoanisole hydrochloride | 42.2 g (0.2 mole) |
| Ammonia (22°Be) | 50 cc |
| Hydrogen peroxide, 20 volumes | 300 cc |
| Water, q.s.p. | 1000 cc |

At the end of 17 hours, concentrated hydrochloric acid is added with agitation until the pH reaches 6.5.

The reaction product is sprayed on the MINOR MOBILE apparatus described in Example 17. The temperature of the air at the inlet is 220°C and the temperature of the air at the outlet is 100°C.

An atomized product is obtained which is soluble in an aqueous alcohol medium.

Chromatography of this atomized product on a thin silica layer shows the presence of bleaches formed by oxidation of the 2,4-diaminoanisole hydrochoride as well as traces of unconverted 2,4-diaminoanisole.

EXAMPLE 21

The solution of Example 20 is allowed to stand in open air at a temperature of about 20°C for 17 hours.

The solution is then neutralized to pH 7 and concentrated so that the volume thereof is reduced by half. This concentration is effected under vacuum at about 45°C.

The solution which is obtained is sprayed in the same manner as in Example 20. A spray product is obtained which is soluble in an aqueous alcohol medium.

The results of chromatography are identical to that to Example 20.

EXAMPLE 22

The following solution is allowed to stand in open air at a temperature of about 20°C for 1 hour:

| | |
|---|---|
| Paratoluylenediamine | 24.4 g (0.2 mole) |
| Resorcin | 11 g (0.1 mole) |
| Metaminophenol | 5.45 g (0.05 mole) |
| Ammonia (22°Be) | 100 cc |
| Hydrogen peroxide, 20 volumes | 500 cc |
| Polyvinylpyrrolidone (MW 40,000) | 50 g |
| Water, q.s.p. | 1000 cc |

At the end of an hour this solution is sprayed directly in a NIRO ATOMIZER apparatus as described in Example 17 with the inlet air temperature being 215°C and the outlet air temperature being 97°C.

The spray product obtained is soluble in an aqueous alcohol medium.

Chromatography on a thin silica layer shows the presence of dyes formed by oxidation and traces of paratoluylenediamine, as well as a larger amount of resorcin and metadiaminophenol.

EXAMPLE 23

The following solution is allowed to stand in open air, at about 20°C, for 15 hours:

| | |
|---|---|
| Paraaminophenol | 10.9 g (0.1 mole) |
| 2,4-diaminoanisole hydrochloride | 21.1 g (0.1 mole) |
| Sodium hydroxide | 4 g (0.1 mole) |
| Anhydrous LSN polypeptide | 50 g |
| Ammonia (22°Be) | 50 cc |
| Hydrogen peroxide, 20 volumes | 500 cc |
| Water, q.s.p. | 1000 cc |

At the end of 15 hours, the solution is sprayed in the apparatus described in Example 17 with the inlet air temperature being 200°C and the outlet air temperature being 85°C. An atomized product is obtained that is soluble in an aqueous alcohol medium.

Chromatography on a thin layer of silica of the atomized product shows the presence of indoaniline and absence of paraaminophenol and metadiaminoanisole.

EXAMPLES 24–34

The procedures outlined in Example 5 are repeated using in comparable amounts the following oxidation bases rather than the paraaminophenol disclosed therein: paraphenylene diamine, N,N-dimethyl paraphenylene diamine, methyl paraphenylene diamine, chloroparaphenylene diamine, 2-methoxy 5-methyl paraphenylene diamine, 2,6-dimethyl 3-methoxy paraphenylene diamine, tetramethyl paraphenylene diamine, 2-methoxy paraphenylene diamine, 2,6-dimethyl paraaminophenol and 2-methyl paraaminophenol. In each instance a lyophilized dye is obtained.

EXAMPLES USING LYOPHILIZED AND SPRAY DRIED DYES

EXAMPLE 35

A colored hair setting lotion is prepared by mixing, at the time of use, 0.125 g of a powder $P_1$ and 25 cc of a solution $S_1$ defined below:

Powder $P_1$:
  Colored spray preparation of Example 20
Solution $S_1$:

| | |
|---|---|
| Copolymer of crotonic acid and vinyl acetate 90/10 (MW 50,000) | 2.0 g |
| Ethyl alcohol | 50 cc |
| Triethanolamine, q.s.p. | pH 7 |
| Water, q.s.p. | 100 cc |

This colored hair setting lotion is applied to hair that has been bleached and dyed blond. After setting and drying, the hair is brilliant, luminous and easy to dress, presenting a very handsome pearly ash sheen.

EXAMPLE 36

A hair setting lotion is prepared by mixing, at the time of use, 0.100 g of a powder $P_2$ and 25 cc of a solution $S_2$ defined below:

Powder $P_2$:

| | |
|---|---|
| Colored spray preparation of Example 20 | 5 g |
| N[(4'-amino 2'-methoxy 3',5'-dimethyl) phenyl]2,6-dimethyl benzoquinone imine | 2 g |
| N[(4'-hydroxy)phenyl] 2,6-dimethyl benzoquinone imine | 30 g |
| Copolymer of polyvinyl pyrrolidone and vinyl acetate 60 : 40: (viscosity 5% in ethanol = 3.3–4 cps). to make up | 100 g |

Solution $S_2$:

| | |
|---|---|
| Copolymer of crotonic acid and vinyl acetate (MW 50,000) | 2 g |
| Ethyl alcohol | 50 cc |
| Camphor benzylidene | 0.2 g |
| Triethanol amine, q.s.p. | pH 8 |
| Water, q.s.p. | 100 cc |

When applied to chestnut colored hair, this hair setting lotion imparts a very pretty mahogany sheen thereto.

EXAMPLE 37

A colored hair setting lotion is prepared by mixing, at the moment of use, 0.100 g of a powder $P_3$ and 25 cc of a solution $S_3$ defined below.

Powder $P_3$:

| | |
|---|---|
| Colored spray prepared as in Example 20 | 1 g |
| Colored spray prepared as in Example 18 | 10 g |
| Copolymer of vinylpyrrolidone and vinyl acetate 60 : 40 q.s.p. (viscosity 5% in ethanol = 3.3–4 cps). | 100 g |

Solution $S_3$:

| | |
|---|---|
| Copolymer of vinyl acetate and crotonic acid (MW 50,000) | 2 g |
| Ethyl alcohol | 50 cc |
| Camphor benzylidene | 0.2 g |
| Butylhydroxyanisole | 0.1 g |
| Triethanolamine, q.s.p. | pH 6 |
| Water, q.s.p. | 100 cc |

When applied to white hair this hair setting lotion imparts thereto a pretty silvery sheen.

EXAMPLE 38

A dye composition is prepared by mixing at the time of use of 0.100 g of a powder $P_4$ and 25 cc of a solution $S_4$ defined below:

Powder $P_4$:
  Colored spray prepared as in Example 17
Solution $S_4$:

| | |
|---|---|
| Hydroxyethyl cellulose sold as "NATROSOL 250 L" by HERCULES POWDER | 0.4 g |
| Ethyl alcohol | 10 cc |
| Citric acid, q.s.p. | pH 4.5 |
| Water, q.s.p. | 100 cc |

When applied to hair that is dyed black, this rinse imparts thereto a pretty bluish sheen that is especially luminous.

EXAMPLE 39

A dye composition is prepared by mixing at the time of use 0.002 g of a powder $P_5$ and 30 cc of a solution $S_5$ defined below.

| | |
|---|---|
| Powder $P_5$: | |
| Colored spray product prepared as in Example 19 | 80 g |
| N[(4'-amino 2'-methoxy 3',5'-dimethyl) phenyl] 2,5-dimethyl benzoquinone imine | 20 g |
| Solution $S_5$: | |
| Ethyl alcohol | 55 cc |
| Hydrogen peroxide, 200 volumes | 5 g |
| Orthophosphoric acid, q.s.p. | pH 3 |
| Water, q.s.p. | 100 cc |

This dye composition is applied to light chestnut hair. After setting and drying, the hair is lightened somewhat, and presents moreover a pretty ash sheen that is particularly handsome.

EXAMPLE 40

A dye composition is prepared that is constituted by mixing at the time of use 0.150 g of powder $P_6$ and 25 cc of a solution $S_6$ defined below.

| | |
|---|---|
| Powder $P_6$: | |
| Colored spray preparation prepared as in Example 22 | |
| Solution $S_6$: | |
| Hydroxyethyl cellulose sold by HERCULES POWDER as "NATROSOL 250 L" | 0.4 g |
| "ETHOMEEN C.15" (corresponding to the condensation of 5 moles ethylene oxide on coconut amine) sold by Armour | 0.10 g |
| Ethyl alcohol | 10 cc |
| Triethanolamine, q.s.p. | pH 4.5 |
| Water, q.s.p. | 100 cc |

This dye composition is applied as a rinse on hair that has a fairly low proportion of white. After setting and drying, the hair is uniform in color and as a whole presents a handsome ash sheen.

EXAMPLE 41

A dye composition is prepared by mixing at the time of use of 0.080 g of powder $P_7$ and 60 cc of a solution $S_6$ defined below.

| | |
|---|---|
| Powder $P_7$: | |
| Colored product of lyophilization prepared as in Example 3 | 90 g |
| Spray product prepared as in Example 20 | 9 g |
| N(4'-amino 2'-methoxy 3',5'-dimethyl phenyl) 2,6-dimethyl benzoquinone imine | 0.3 g |
| N(4'-hydroxy phenyl)2,6-dimethyl benzoquinone imine | 0.7 g |
| Solution $S_6$: | |
| The same as in Example 40 | |

This dye composition is applied to freshly bleached hair. After setting and drying, the hair has a very light blond hue that is especially luminous.

EXAMPLE 42

A dye composition is prepared by mixing at the time of use 0.100 g of powder $P_8$ and 25 cc of solution $S_7$ defined below:

| | |
|---|---|
| Powder $P_8$: | |
| Color spray product defined in Example 18 | 5 g |
| 4-methyl 2,3-dihydroxyethylamino beta morpholino phenoxazonium bromide | 5 g |
| Copolymer of vinyl pyrrolidone and vinyl acetate 60 : 40 q.s.p. (viscosity 5% in ethanol = 3,3–4 cps.) | 100 g |
| Solution $S_7$: | |
| Copolymer of vinyl pyrrolidone and vinyl acetate 60 : 40 (viscosity 5% in ethanol = 3,4–4 cps). | 3 g |
| Triethanolamine, q.s.p. | pH 8 |
| Water, q.s.p. | 100 cc |

This hair set lotion, applied to natural black hair, imparts thereto a very luminous blue sheen.

EXAMPLE 43

A dye composition is prepared by mixing at the time of use 0.050 g of powder $P_9$ and 25 cc of a solution $S_8$ defined below.

| | | |
|---|---|---|
| Powder $P_9$: | | |
| Spray preparation as in Example 20 | 40 | g |
| Spray preparation prepared as in Example 23 | 60 | g |
| Solution $S_8$: | | |
| Copolymer of crotonic acid and vinyl acetate (MW 50,000) | 2 | g |
| Ethyl alcohol | 20 | g |
| Carbopol 940 (carboxyvinyl polymer, carboxypolymethylene) sold by B.F. GOODRICH | 0.4 | g |
| Triethanolamine | 0.8 | g |
| Water, q.s.p. | 100 | g |

This hair setting lotion which is a gel is applied on hair that has been bleached and dyed golden blond. After drying, the hair has a very handsome pearly blond hue.

EXAMPLE 44

A dye composition is prepared by mixing at the time of use 0.0002 g of a powder $P_{10}$ and 10 cc of a solution $S_9$ described below:

| | |
|---|---|
| Powder $P_{10}$: | |
| Colored spray product prepared as in Example 18. | |
| Solution $S_9$: | |
| Ethyl alcohol | 96 cc |
| Water, q.s.p. | 100 cc |

This lotion is applied to hair that contains some white. After drying the white hair is brilliant and presents a silvery sheen that is very luminous and especially handsome.

EXAMPLE 45

A dye composition is prepared by mixing at the time of use 0.3 g of a powder $P_{11}$ and 25 cc of a solution $S_{10}$ defined below.

| Powder P₁₁: | |
|---|---|
| Spray product prepared as in Example 20 | 75 g |
| Spray product prepared as in Example 17 | 25 g |

| Solution S₁₀: | |
|---|---|
| Butyl Cellosolve | 8 g |
| Propylene glycol | 8 g |
| Polyethoxyether of alkyl phenol sold as "REMCOPAL 334" by GERLAND | 22 g |
| Polyethoxyether of alkyl phenol sold as "REMCOPAL 349" by GERLAND | 22 g |
| Ammonia (22°Be) | 10 g |
| Water, q.s.p. | 100 g |

Twenty grams hydrogen peroxide, 20 volumes, are added to 20 grams of the above solution. A gel is obtained that is applied to chestnut hair. After 30 minutes the hair is washed. After drying, the hair exhibits a pearly blond hue.

EXAMPLE 46

A colored hair setting lotion is prepared by mixing at the time of use 0.3 grams of powder $P_{12}$ and 30 cc of a solution $S_{11}$ defined below:

| Powder P₁₂: | |
|---|---|
| Spray preparation of Example 23 | 50 grams |
| Spray preparation of Example 20 | 50 grams |

| Solution S₁₁: | |
|---|---|
| Ethanol | 10 cc |
| Ammonia (22°Be) | 5 g |
| Hydrogen peroxide, 20 volumes | 50 g |
| Water, q.s.p. | 100 cc |

This hair setting lotion is applied to dark blond hair for 15 minutes. The hair is then washed and set. After drying, the hair has a golden blond hue.

EXAMPLE 47

A colored hair setting lotion is prepared at the time of use by mixing 0.10 gram of powder $P_{13}$ and 25 cc of a solution $S_{12}$ defined below.

| Powder P₁₃: | |
|---|---|
| Spray preparation as in Example 19 | 70 g |
| N 1-methylamino 4-amino propylamino anthraquinone | 30 g |

| Solution S₁₂: | |
|---|---|
| Copolymer of crotonic acid and vinyl acetate (MW 50,000) | 2.0 g |
| Ethanol | 50 cc |
| Camphor benzylidene | 0.2 g |
| Triethanolamine, q.s.p. | pH 7 |
| Water, q.s.p. | 100 cc |

When applied to hair dyed black, this hair setting lotion imparts thereto a very luminous blue sheen.

EXAMPLE 48

The following dye composition is prepared:

| Colored product of lyophilization prepared as in Example 1 | 0.1 | g |
|---|---|---|
| "Ethomeen C" (condensation product of 5 molecules ethylene oxide on coconut amine) sold by Armour | 0.15 | g |
| Triethanolamine, q.s.p. | pH | 7 |
| Water, q.s.p. | 100 | g |

Twenty cc of this lotion are applied to bleached hair and left in contact therewith for 20 minutes. Thereafter, the hair is washed and dried and then set and dried.

The hair thus treated is brilliant, easy to comb and dyed rosy beige.

EXAMPLE 49

A colored hair setting lotion is prepared, having the following composition:

| Lyophilized powder as in Example 2 | 0.1 | g |
|---|---|---|
| Copolymer of crotonic acid and vinyl acetate 90:10 (MW 50,000) | 2.0 | g |
| Ethyl alcohol | 50 | ml |
| Triethanolamine, q.s.p. | pH | 7 |
| Water, q.s.p. | 100 | ml |

Twenty cc of this solution are applied to bleached hair and the hair is then set. After drying the hair, which has an ashy light blond hue, is brilliant and easily dressed.

EXAMPLE 50

The following dye-bleach lotion is prepared:

| Lyophilized powder of Example 1 | 0.5 | g |
|---|---|---|
| 20% ammonia solution | 10 | ml |
| Water, q.s.p. | 100 | ml |

Ten ml of hydrogen peroxide, 20 volumes, are added to 10 ml of this solution and the mixture is applied to chestnut hair for 30 minutes. The hair is then rinsed, washed and dried and exhibits a pearly blond hue.

EXAMPLE 51

A dye composition is prepared by mixing at the time of use 0.08 g of a powder $P_{14}$ and 25 cc of a solution $S_{14}$ defined below.

| Powder P₁₄: | | |
|---|---|---|
| Lyophilized product of Example 3 | 99.6 | g |
| N-[(4'-amino 2'-methoxy 3'5'-dimethyl) phenyl] 2,6-dimethyl benzoquinone imine | 0.4 | g |

| Solution S₁₄: | | |
|---|---|---|
| Hydroxyethyl cellulose sold under the tradename "Natrosol 250 L" by "Hercules Powder" | 0.4 | g |
| Ethyl alcohol | 10 | g |
| Citric acid, q.s.p. | pH | 4.5 |
| Water, q.s.p. | 100 | cc |

This composition is applied as a mixture to bleached, light blond dyed hair. After setting and drying, the hair is brilliant, luminous and readily dressed, and has a very handsome ashy beige sheen.

EXAMPLE 52

A dye composition is prepared by mixing at the time of use 0.03 g of a powder $P_{15}$ and 25 cc of a solution $S_{15}$ defined below.

| Powder P₁₅: | | |
|---|---|---|
| Colored product of lyophilization prepared as in Example 3 | 99 | g |
| N-[4'-amino 2'-methoxy 3',5'-dimethyl) phenyl] 2,6-dimethylbenzoquinone imine | 0.3 | g |
| N(4'-hydroxyphenyl) 2,6-dimethyl-benzoquinone imine | 0.7 | g |

-continued

| Solution $S_{15}$: | | |
|---|---|---|
| Hydroxyethyl cellulose sold under the tradename "Natrosol 250 L" by "Hercules Powder" | 0.4 | g |
| "Ethomeen C" (corresponding to the condensation of 5 moles ethylene oxide on coconut amine) sold by Armour | 0.10 | g |
| Ethyl alcohol | 10 | g |
| Triethanolamine, q.s.p. | pH | 6 |
| Water, q.s.p. | 100 | g |

This rinse is applied to freshly bleached hair. After setting and drying, the hair has a particularly luminous very light blond hue.

EXAMPLE 53

A colored hair setting lotion is prepared by mixing at the time of use 0.1 g of a powder $P_{16}$ and 25 cc of a solution $S_{16}$ defined below:

| Powder $P_{16}$: | | |
|---|---|---|
| Colored product of lyophilization prepared as in Example 9 | 50 | g |
| 4-methyl 8-di-beta-hydroxyethylamino [2,3-β]morpholino phenoxazonium bromide | 5 | g |
| Copolymer of vinyl pyrrolidone and vinyl acetate 60 : 40 q.s.p. (viscosity 5% in ethanol = 3,3–4 cps). | 100 | g |

| Solution $S_{16}$: | | |
|---|---|---|
| Copolymer of vinyl pyrrolidone and vinyl acetate 60 : 40 (viscosity 5% in ethanol = 3,3–4 cps). | 2.0 | g |
| Triethanolamine, q.s.p. | pH | 8 |
| Water, q.s.p. | 100 | cc |

This hair setting lotion applied to naturally black hair imparts thereto a very luminous bluish sheen.

EXAMPLE 54

A colored hair setting lotion is prepared by mixing at the time of use 0.07 g of a powder $P_{17}$ and 25 cc of a solution $S_{17}$ defined below.

| Powder $P_{17}$ | | |
|---|---|---|
| Colored product of lyophilization prepared as in Example 5 | 70 | g |
| Nitroparaphenylene diamine | 30 | g |

| Solution $S_{17}$: | | |
|---|---|---|
| Copolymer of crotonic acid and vinyl acetate (MW 50,000) | 2.0 | g |
| N-acetylethanol amine | 0.1 | g |
| Citric acid, q.s.p. | pH | 4 |
| Water, q.s.p. | 100 | cc |

This hair setting lotion is applied to hair that has been bleached and dyed auburn. After drying the hair has a very luminous mahogany color. Moreover, the hair is brilliant and readily dressed.

EXAMPLE 55

A colored hair setting lotion is prepared at the time of use by mixing 0.15 g of a powder $P_{18}$ and 25 cc of a solution $S_{18}$ defined below.

| Powder $P_{18}$: | | |
|---|---|---|
| Colored lyophilization product prepared as in Example 6 | 80 | g |
| N-1-methylamino 4-gamma-aminopropyl-amino anthraquinone | 20 | g |

| Solution $S_{18}$: | | |
|---|---|---|
| Copolymer of crotonic acid and vinyl acetate (MU 50,000) | 2.0 | g |
| Ethanol | 50 | cc |
| Camphor benzylidene | 0.2 | g |
| Triethanolamine, q.s.p. | pH | 9 |
| Water, q.s.p. | 100 | cc |

When applied to hair that has been dyed black, this hair setting lotion imparts thereto a lightly greenish blue sheen that is very luminous.

EXAMPLE 56

A colored hair setting lotion is prepared at the time of use by mixing 0.35 g of a powder $P_{19}$ precompressed to form a tablet and 25 cc of a solution $S_{19}$ described below:

| Powder $P_{19}$: | | |
|---|---|---|
| Colored lyophilization product prepared as in Example 3 | 20 | g |
| Colored lyophilization product prepared as in Example 4 | 66 | g |
| Colored lyophilization product prepared as in Example 13 | 14 | g |

| Solution $S_{19}$: | | |
|---|---|---|
| Copolymer of crotonic acid and vinyl acetate (MW 50,000) | 2.0 | g |
| Ethyl alcohol | 50 | cc |
| Camphor benzylidene | 0.2 | g |
| Butylhydroxyanisole | 0.1 | g |
| Triethanolamine, q.s.p. | pH | 7 |
| Water, q.s.p. | 100 | cc |

When applied to wet, bleached, chestnut dyed hair, this hair setting lotion imparts thereto a very luminous chestnut brown hue. The hair is brilliant and easily dressed.

EXAMPLE 57

A colored hair setting lotion is prepared at the time of use by mixing 0.004 g of a powder $P_{20}$ and 25 cc of a solution $S_{20}$ defined below.

| Powder $P_{20}$: | | |
|---|---|---|
| Colored product of lyophilization prepared as in Example 4 | 80 | g |
| Colored product of lyophilization prepared as in Example 3 | 20 | g |

| Solution $S_{20}$: | | |
|---|---|---|
| Copolymer of crotonic acid and vinyl acetate (MW 50,000) | 2.0 | g |
| Ethyl alcohol | 50 | cc |
| Hydrogen peroxide, 200 volumes | 5 | g |
| Orthophosphoric acid, q.s.p. | pH | 3 |
| Water, q.s.p. | 100 | cc |

This hair setting lotion is applied to naturally light brown hair. After setting and drying, the hair is lightly brightened and has an especially handsome luminous pearly sheen.

EXAMPLE 58

A colored hair setting lotion is prepared by mixing at the time of use 0.002 g of a powder $P_{21}$ and 25 cc of a solution $S_{21}$ defined below.

| Powder $P_{21}$: | | |
|---|---|---|
| Colored product of lyophilization prepared as in Example 14 | 50 | g |

| | | |
|---|---|---|
| Copolymer of vinyl pyrrolidone and vinyl acetate 60 : 40 (viscosity 5% = 3.3–4 cps) q.s.p. | 100 | g |
| Solution $S_{21}$: | | |
| Copolymer of vinyl pyrrolidone and vinyl acetate 60 : 40 (viscosity 5% in ethanol = 3,3–4 cps). | 2.0 | g |
| Butyl Cellosolve | 0.2 | g |
| Ethyl alcohol | 50 | cc |
| N-acetylethanol amine | 0.10 | g |
| Camphor benzylidene | 0.2 | g |
| Butylhydroxy anisole | 0.15 | g |
| Triethanolamine, q.s.p. | pH | 7 |
| Water, q.s.p. | 100 | cc |

When this hair setting lotion is applied to very pale blond hair it imparts thereto a very luminous ashy sheen.

EXAMPLE 59

A dye composition is prepared at the time of use by mixing 0.3 g of a powder $P_{22}$ and 50 cc of a solution $S_{22}$ defined below.

| | | |
|---|---|---|
| Powder $P_{22}$: | | |
| Colored product of lyophilization prepared as in Example 3 | 95 | g |
| Colored product of lyophilization prepared as in Example 13 | 5 | g |
| Solution $S_{22}$: | | |
| Hydroxyethyl cellulose sold under the tradename "Natrosol 250 L" by Hercules Powder Co. | 0.4 | g |
| Citric acid, q.s.p. | pH | 3.5 |
| Water, q.s.p. | 100 | cc |

This rinse composition is applied to dark chestnut hair in which there are some white hairs. After setting and drying, the white hairs are masked and the hair as a whole has a very uniform ashy sheen that is expecially handsome.

EXAMPLE 60

A gel hair setting lotion is prepared at the time of use by mixing 0.08 g of a powder $P_{23}$ and 25 cc of a solution $S_{23}$ defined below.

| | | |
|---|---|---|
| Powder $P_{23}$: | | |
| Colored product of lyophilization prepared as in Example 4 | 20 | g |
| Colored product of lyophilization prepared as in Example 3 | 80 | g |
| Solution $S_{23}$: | | |
| Copolymer of crotonic acid and vinyl acetate (MW 50,000) | 2 | g |
| Ethyl alcohol | 20 | g |
| Carbopol 940 (carboxyvinyl polymer-carboxy polymethylene) sold by B.F. Goodrich | 0.4 | g |
| Triethanolamine | 0.8 | g |
| Water, q.s.p. | 100 | g |

This hair setting lotion is applied to bleached hair that has been dyed golden blond. After drying the hair has a very handsome pearly blond hue.

EXAMPLE 61

A colored hair setting lotion is prepared at the time of use by mixing 0.3 g of a powder $P_{24}$ and 25 cc of a solution $S_{24}$ defined below.

| | | |
|---|---|---|
| Powder $P_{24}$: | | |
| Colored lyophilization product prepared as in Example 15 | 100 | g |
| Solution $S_{24}$: | | |
| Ethanol | 10 | g |
| Ammonia (22°Be) | 5 | g |
| Hydrogen peroxide, 20 volumes | 50 | g |
| Water, q.s.p. | 100 | g |

This hair setting lotion is applied for 15 minutes to dark blond hair. The hair is then washed and set. After drying the hair has an ashy blond hue.

EXAMPLE 62

A gel dye composition is prepared at the time of use by mixing 0.3 g of a powder $P_{25}$ and 25 cc of a solution $S_{25}$ described below.

| | | |
|---|---|---|
| Powder $P_{25}$: | | |
| Colored product of lyophilization prepared as in Example 15 | 75 | g |
| Colored product of lyophilization prepared as in Example 3 | 25 | g |
| Solution $S_{25}$: | | |
| Butyl Cellosolve | 8 | g |
| Propylene glycol | 8 | g |
| Polyethoxyether of alkyl phenol sold under the tradename "Remcopal 334" by the Gerland Co. | 22 | g |
| Polyethoxyether of alkyl phenol sold under the tradename "Remcopal 349" by Gerland | 22 | g |
| Ammonia (22°Be) | 10 | g |
| Water, q.s.p. | 100 | g |

Ten grams hydrogen peroxide, 20 volumes, are added to 10 grams of the solution thus prepared. A gel is thus obtained that is applied to chestnut hair. After 30 minutes the hair is washed. After dying it has an ash blond hue.

EXAMPLE 63

A dye composition is prepared at the time of use by mixing 0.0002 g of a powder $P_{26}$ and 10 cc of a solution $S_{26}$ defined below.

| | | |
|---|---|---|
| Powder $P_{26}$: | | |
| Colored lyophilization product prepared as in Example 13 | | |
| Solution $S_{26}$: | | |
| Ethyl alcohol | 96 | g |
| Water, q.s.p. | 100 | g |

This lotion is applied to hair in which there is some white. After drying, the white hair is brilliant and has a very luminous and especially handsome silvery sheen.

EXAMPLE 64

A colored hair setting lotion is prepared at the time of use by mixing 0.2 g of the colored product of lyophilization prepared as in Example 3 and 25 cc of a solution $S_{27}$ defined below.

| | | |
|---|---|---|
| Solution $S_{27}$: | | |
| Copolymer of crotonic acid and vinyl acetate 90:10 (MW 50,000) | 2.0 | g |
| Ethyl alcohol | 50 | cc |
| Triethanolamine, q.s.p. | pH | 7 |

-continued

| Water, q.s.p. | 100 g |

This hair setting lotion is applied to naturally blond hair. After drying, the hair has a very luminous pearly sheen that is especially handsome.

EXAMPLE 65

A dye composition is prepared at the time of use by mixing 0.1 g of a powder P28 and 25 cc of a solution S28.

| POWDER P28 | |
|---|---|
| Colored lyophilization product prepared as in example 3 | 95 g |
| N-[(4'-amino 2'-methoxy 5'-methyl) phenyl]2-aza 3-aminobenzoquinonediimine mono acetate | 5 g |
| SOLUTION S28 | |
| Copolymer of crotonic acid and vinyl acetate 90 : 10 (M.W. 50,000) | 2 g |
| Ethyl alcohol | 50 cc |
| Triethanolamine q.s.p. | pH 7 |
| Water q.s.p. | 100 g |

This hair setting lotion is applied to hair that has been dyed blond. After drying the hair has a very handsome ashy blond hue particularly aesthetical.

What is claimed is

1. A process for producing a lyophilized dyestuff comprising reacting with a molar excess of hydrogen peroxide an oxidation base in an aqueous alkaline solution open to ambient atmosphere and having a pH ranging from 8 to 13 at a temperature between about 15°–30°C for a period of about 5 minutes to 30 hours and lyophilizing said raction mixture, said oxidation base being selected from the group consisting of paratoluylene diamine, paraphenylene diamine, N,N-dimethyl paraphenylene diamine, chloroparaphenylene diamine, 2-methoxy-5-methyl paraphenylene diamine, 2,6-dimethyl-3methoxy paraphenylene diamine, tetramethyl paraphenylene diamine, 2-methoxy paraphenylene diamine, para aminophenol, 2,6-dimethyl para aminophenol, 2,4-diamino anisole, 2-methyl para aminophenol, the hydrochlorides thereof, and mixtures thereof, wherein lyophilizing said reaction mixture comprises freezing said reaction mixture at a temperature of about −200°C to −60°C and subliming said frozen mixture at a temperature of about −50°C to −30°C at a pressure of about 0.01 mm Hg to 0.1 mm Hg.

2. The process of claim 1 which also includes desorbing the lyophilized reaction product at a temperature ranging between 15°–60°C at a pressure of about 0.01 mm Hg to eliminate therefrom any residual moisture content.

3. The process of claim 1 wherein said aqueous alkaline solution is an aqueous ammoniacal solution.

4. The process of claim 1 wherein said oxidation base and said hydrogen peroxide are reacted in the presence of a coupler selected from the group consisting of metaphenylene diamine, 2,4-diamino toluene, metal aminophenol, 6-methyl-3-aminophenol, N-methyl meta aminophenol, 4-methoxy-3-aminophenol, resorcin, α-naphthol, 3-methoxy-4-aminophenol and the sulfate, hydrochloride and hydrobromide thereof, the molar ratio of said coupling agent to said oxidation base before oxidation being between 0:1 and 10:1.

5. The process of claim 4 wherein the molar ratio of said coupler to said oxidation base before oxidation is between 0:1 and 2:1.

6. The process of claim 1 wherein said hydrogen peroxide and said oxidation base are reacted in the presence of a filler selected from the group consisting of hydrolysis products of proteins, alanine, glycine, glutamic acid, cystine, polyvinyl pyrrolidone having a molecular weight ranging between 40,000 to 360,000, a copolymer of polyvinyl pyrrolidone and vinyl acetate having a molecular weight ranging between 40,000 to 160,000 wherein the weight ratio of polyvinyl pyrrolidone to vinyl acetate is 70%:30% to 30%:70% and a copolymer of crotonic acid and vinyl acetate having a molecular weight of 40,000 to 200,000 wherein the weight ratio of crotonic acid to vinyl acetate is 90%:10%, said filler being present in amounts of 1-20 percent by weight of the total reaction mixture.

7. A dye in powder form made in accordance with the process of claim 1.

8. A process for producing a spray-dried dye comprising reacting an oxidation base with a molar excess of hydrogen peroxide in an aqueous alkaline solution open to ambient atmosphere and having a pH ranging from 8 to 13 at a temperature between about 15°–30°C for a period of about 5 minutes to 30 hours and spray drying said reaction mixture, said oxidation base being selected from the group consisting of paratoluylene diamine, paraphenylene diamine, N,N-dimethyl paraphenylene diamine, chloroparaphenylene diamine, 2-methoxy5-methyl paraphenylene diamine, 2,6-dimethyl-3-methoxy paraphenylene diamine, tetramethyl paraphenylene diamine, 2-methoxy paraphenylene diamine, para aminophenol, 2,6-dimethyl para aminophenol, 2,4-diamino anisole, 2-methyl para aminophenol, the hydrochlorides thereof, and mixtures thereof, wherein spray drying said reaction mixture comprises introducing said reaction mixture into a current of air having an inlet temperature between 80°–350°C and an outlet temperature between about 50°–200°C.

9. The process of claim 8 wherein the inlet air temperature ranges between 150°–300°C and the outlet air temperature ranges between 80°–130°C.

10. The process of claim 8 wherein the inlet air temperature is about 300°C and the outlet air temperature is about 100°C.

11. The process of claim 8 wherein said aqueous alkaline solution is an aqueous ammoniacal solution.

12. The process of claim 8 wherein said hydrogen peroxide and said oxidation base are reacted in the presence of a coupler selected from the group coonsisting of metaphenylene diamine, 2,4-diamino toluene, meta aminophenol, 4-methoxy-3aminophenol, resorcin, α-naphthol, 3-methoxy-4-aminophenol and the sulfate, hydrochloride and hydrobromide thereof, the molar ratio of said coupler to said oxidation base before oxidation being between 0:1 to 10:1.

13. The process of claim 12 wherein the molar ratio of said coupler to said oxidation base before oxidation is between 0:1 and 2:1.

14. The process of claim 8 wherein said hydrogen peroxide and said oxidation base are reacted in the presence of a filler selected from the group consisting of hydrolysis products of proteins, alanine, glycine, glutamic acid, cystine, polyvinyl pyrrolidone having a molecular weight ranging between 40,000 to 360,000, a copolymer of polyvinyl pyrrolidone and vinyl acetate having a molecular weight ranging between 40,000 to 160,000 wherein the weight ratio of polyvinyl pyrrolidone to vinyl acetate is 70%:30% to 30%:70% and a copolymer of crotonic acid and vinyl acetate having a molecular weight of 50,000 to 200,000 wherein the weight ratio of crotonic acid to vinyl acetate is 90%:10%, said filler being present in amounts of 1–20 percent by weight of the total reaction mixture.

15. A dye in powder form made in accordance with the process of claim 8.

16. A two component pack which comprises, as the first component, a dye made in accordance with the process of claim 1 and as the second component a cosmetic carrier for said dye, said carrier comprising a member selected from the group consisting of water, lower alkanol selected from the group consisting of ethanol and isopropanol and an aqueous solution of said lower alkanol containing 1–96 weight percent of said lower alkanol.

17. A two component pack which comprises, as the first component a dye made in accordance with the process of claim 8 and as the second component a cosmetic carrier for said dye, said carrier comprising a member selected from the group consisting of water, lower alkanol selected from the group consisting of ethanol and isopropanol and an aqueous solution of said lower alkanol containing 1–96 weight percent of said lower alkanol.

* * * * *

UNITED STATES PATENT OFFICE
CERTIFICATE OF CORRECTION

Patent No. 3,960,476          Dated  June 1, 1976

Inventor(s) Giuliana Ghilardi, et al

It is certified that error appears in the above-identified patent and that said Letters Patent are hereby corrected as shown below:

In the Heading

The foreign application priority data should read:

--March 3, 1970     Luxemburg        60,449

October 19, 1970  Luxemburg        61,890

February 15, 1971 Luxemburg        62,596--

Signed and Sealed this

Second Day of November 1976

[SEAL]

Attest:

RUTH C. MASON
*Attesting Officer*

C. MARSHALL DANN
*Commissioner of Patents and Trademarks*

UNITED STATES PATENT OFFICE
CERTIFICATE OF CORRECTION

Patent No. 3,960,476    Dated   June 1, 1976

Inventor(s) Giuliana Ghilardi et al

It is certified that error appears in the above-identified patent and that said Letters Patent are hereby corrected as shown below:

IN THE HEADING

Please insert:

--[73 Assignee: L'Oreal, Paris, France--

Signed and Sealed this

Eighth Day of February 1977

[SEAL]

Attest:

RUTH C. MASON
Attesting Officer

C. MARSHALL DANN
Commissioner of Patents and Trademarks